United States Patent
Yachia et al.

(10) Patent No.: US 9,782,277 B2
(45) Date of Patent: Oct. 10, 2017

(54) SYSTEM AND METHOD FOR MANUFACTURING A STENT

(75) Inventors: Daniel Yachia, Herzliya (IL); Ziv Kalfon, Haifa (IL)

(73) Assignee: ALLIUM MEDICAL SOLUTIONS LTD., Caesarea Industrial Park-South (IL)

( * ) Notice: Subject to any disclaimer, the term of this patent is extended or adjusted under 35 U.S.C. 154(b) by 694 days.

(21) Appl. No.: 14/007,418

(22) PCT Filed: Apr. 4, 2012

(86) PCT No.: PCT/IL2012/050124
§ 371 (c)(1),
(2), (4) Date: Sep. 25, 2013

(87) PCT Pub. No.: WO2012/137206
PCT Pub. Date: Oct. 11, 2012

(65) Prior Publication Data
US 2014/0015163 A1  Jan. 16, 2014

Related U.S. Application Data

(60) Provisional application No. 61/471,519, filed on Apr. 4, 2011.

(51) Int. Cl.
*A61F 2/82* (2013.01)
*B29C 41/08* (2006.01)
(Continued)

(52) U.S. Cl.
CPC .............. *A61F 2/82* (2013.01); *B05B 7/0075* (2013.01); *B05B 13/0235* (2013.01);
(Continued)

(58) Field of Classification Search
CPC ................ A61F 2002/9528; A61F 2/82; A61F 2240/001; A61F 2250/0071;
(Continued)

(56) References Cited

U.S. PATENT DOCUMENTS 5,234,457 A * 8/1993 Andersen .................. A61F 2/90
606/154
5,827,321 A * 10/1998 Roubin ...................... A61F 2/91
606/195

(Continued)

FOREIGN PATENT DOCUMENTS

WO  9304720 A1  3/1993
WO  03099166 A1  12/2003

*Primary Examiner* — Nahida Sultana
(74) *Attorney, Agent, or Firm* — Browdy and Neimark, PLLC

(57) ABSTRACT

The invention provides a system (1) and method for manufacturing a stent. A spraying device (14) sprays a polymeric suspension (16) onto a mandrel (4). During spraying of the polymeric suspension (16) onto the mandrel (4), the mandrel (4) is manipulated by a micromanipulator (8) to produce a continuous coating on the mandrel (4) having a nonuniform thickness. The polymeric coating is allowed to cure on the mandrel (4) to form the stent, which is then removed from the mandrel (4). The method can comprise embedding a filament (2) in the polymeric coating and incorporating one or more drugs in the stent.

15 Claims, 3 Drawing Sheets

(51) Int. Cl.
  *B05B 7/00* (2006.01)
  *B05B 13/02* (2006.01)
  *A61F 2/95* (2013.01)
  *B29L 31/00* (2006.01)
(52) U.S. Cl.
  CPC .... *B29C 41/085* (2013.01); *A61F 2002/9528* (2013.01); *A61F 2230/0091* (2013.01); *A61F 2240/001* (2013.01); *A61F 2250/0071* (2013.01); *B29L 2031/7534* (2013.01)
(58) Field of Classification Search
  CPC ........... A61F 2230/0091; B05B 7/0075; B05B 13/0235; B29C 41/085; B29L 2031/7534
  USPC ..... 623/1.15, 2.24, 920, 23.7; 264/309–310; 424/423
  See application file for complete search history.

(56) References Cited

U.S. PATENT DOCUMENTS

| | | | |
|---|---|---|---|
| 6,030,371 A | 2/2000 | Pursley | |
| 7,313,907 B2* | 1/2008 | Fare' | D04H 3/16 57/350 |
| 7,323,209 B1* | 1/2008 | Esbeck | B05D 3/0254 427/2.25 |
| 7,470,389 B2* | 12/2008 | Berrigan | D01D 5/0985 156/167 |
| 7,959,999 B2 | 6/2011 | Prabhu | |
| 8,119,151 B2 | 2/2012 | Heidner et al. | |
| 8,535,590 B2* | 9/2013 | Milner | B29C 41/003 264/309 |
| 2002/0081732 A1 | 6/2002 | Bowlin et al. | |
| 2003/0042651 A1* | 3/2003 | Najour | D01D 5/098 264/211.14 |
| 2003/0230823 A1 | 12/2003 | Bartholomew | |
| 2004/0086542 A1* | 5/2004 | Hossainy | A61L 27/34 424/423 |
| 2006/0240065 A1* | 10/2006 | Chen | A61F 31/10 424/423 |
| 2007/0259099 A1* | 11/2007 | Van Sciver | B05D 1/02 427/2.24 |
| 2008/0260936 A1* | 10/2008 | Heidner | B05D 1/002 427/2.25 |
| 2009/0035449 A1* | 2/2009 | Chen | A61F 2/91 427/2.25 |
| 2009/0061072 A1* | 3/2009 | Isch | A61F 2/88 427/2.25 |
| 2009/0192593 A1 | 7/2009 | Meyer | |
| 2009/0259294 A1 | 10/2009 | Cully et al. | |
| 2010/0049296 A1* | 2/2010 | Sarasam | A61F 31/10 623/1.11 |
| 2012/0029616 A1 | 2/2012 | Guerriero et al. | |
| 2012/0258270 A1* | 10/2012 | Chang | B29C 33/62 428/36.92 |
| 2013/0013054 A1* | 1/2013 | Clarke | A61F 2/07 623/1.15 |
| 2015/0238335 A1* | 8/2015 | Kim | B23K 26/402 623/1.15 |

* cited by examiner

SYSTEM AND METHOD FOR MANUFACTURING A STENT

FIELD OF THE INVENTION

This invention relates to systems and methods for producing medical devices.

BACKGROUND OF THE INVENTION

Many indwelling medical devices have a hollow portion. For example, stents are hollow devices that are inserted into body ducts for preventing narrowing of the duct lumen, for tutoring a dilated lumen or for acting as a substrate for tissue growth. As another example, a catheter may have a hollow portion that may serve to transfer a fluid from outside the body to a body cavity, or for draining fluid from a body cavity. As yet another example, an artificial blood vessel valve has a casing enclosing a space through which blood flows.

International Patent Publication WO03/099166 discloses an indwelling unravable medical device having a hollow portion, such as a stent. The device has a generally helical seam which is a weakened region in the wall of the device. When it is desirable to remove the indwelling device from the body, an end of the device is grasped and pulled. As the end is pulled, the seam splits so that the device is removed as a slender strip of material.

U.S. Pat. No. 8,119,151 to Heidner et al discloses a method for coating portions of a medical device. A layer of coating is applied to a surface of a medical device with an applicator. While the coating is being applied, the spreader is positioned in contact with the coating to reduce the coating thickness by spreading the coating over a larger surface area of the target surface.

US Patent Publication 20120029616 of Guerriero et al discloses a method of coating a stent in which the flow rate of a coating material sprayed onto the stent is varied while axially moving the stent. The stent repeatedly passes from one end of the stent to another relative to a major axis of the stent adjacent to a fixed or movable spray nozzle. The axial speed may be varied during spraying of the stent based on the modified flow rate of the coating material to deposit a selected amount of coating material per pass.

U.S. Pat. No. 7,959,999 to Prabhu discloses a stent formed by encasing or encapsulating metallic rings in an inner polymeric layer and an outer polymeric to layer. At least one polymer link connects adjacent metallic rings. The stent is drug loaded with one or more therapeutic agents or drugs.

US Patent Publication 20090259294 to Cully et al discloses a removable device such as a stent-graft, intended for applications where it may be desirable to remove the device at some time following implantation. The stent-graft includes a helically-wound stent provided with a covering of graft material. It is removable by gripping an end of the helically-wound stent component with a retrieval device and applying tension to the stent component in the direction in which it is intended to be withdrawn from the site of implantation.

US Patent Publication 20090192593 to Meyer et al discloses implantable medical devices, such as a stent, for delivering a therapeutic agent, and methods for making such medical devices. In one embodiment, the medical device comprises a stent having a plurality of struts, at least one of which has a cavity disposed therein. A therapeutic agent is delivered from the cavity through and opening in a strut surface.

SUMMARY OF THE INVENTION

The present invention provides a system and method for manufacturing a stent. The system of the invention includes a mandrel and a micromanipulator that generates a longitudinal movement and a rotational movement of the mandrel. The system also includes a spraying device that sprays a polymeric coating material such as a polymeric suspension onto the mandrel During spraying of the polymeric suspension onto the mandrel, the mandrel is manipulated by a micromanipulator to produce a continuous coating on the mandrel not having any holes or breaks therein. At least one of the flow rate of the liquid streams, the width of the liquid streams, a velocity of the linear movement of the mandrel and a rotational velocity of the mandrel is varied during manipulation of the mandrel, so that a continuous coating is produced having a non-constant thickness. The polymeric coating is allowed to cure on the mandrel to form the stent, which is then removed from the mandrel.

In one embodiment of the invention, the mandrel is manipulated to produce a stent having a helical groove on the outer surface of the stent. The helical groove is a weakened region in the stent that forms a tear line. When it is desired to remove the stent from the body, the end of the stent can be grasped by a grasping device and pulled. As the end is pulled, the tear line splits so that the stent is removed from the body as a slender strip.

In the manufacture of a medical device by the method of the invention, application of the polymer suspension to the filament may be carried out in a single application step, as described above. Alternatively, two or more application steps may be used, in which at least one of the applications involves spraying polymer suspension, using the system of the invention. For example, a first coat may be sprayed onto the mandrel producing a coating having a smooth outer surface, and then a second coat may be applied having a grooved outer surface. As another example, a first coat of polymer suspension may be applied by dipping the mandrel and filament into a polymer suspension, and then spraying a second coat using the system of the invention. When more than one polymer applications are used, the different coats may be from the same material or from different materials.

After formation of the stent of the medical device, the device may be adapted, for example, to contain one or more drugs that are released over time after deployment of the device in the body. For example, a small region of the polymer can be removed and replaced with a plug contain the drug or drugs to be released.

Thus, in one of its aspects, the present invention provides a system for manufacturing a stent comprising:
  (a) a spraying device configured to deliver one or more liquid streams, each liquid stream having a flow rate and a width;
  (b) a mandrel having a longitudinal axis;
  (c) a micromanipulator configured to grasp the mandrel and to manipulate the mandrel in the liquid streams; and
  (d) a processor configured to
    (a) activate the micromanipulator to manipulate the mandrel in the one or more liquid streams according to a predetermined pattern of movement of the mandrel, the predetermined pattern of movement having a linear movement of the mandrel along the longitudinal axis and further having a rotational movement of the mandrel around the longitudinal axis; and (b) activate the spraying device to spray the one or more liquid streams onto the mandrel as the mandrel is being manipulated in the liquid streams to form a continuous coating over the mandrel;

wherein at least one of the flow rate of the liquid streams, the width of the liquid streams, a velocity of the linear movement of the mandrel and a rotational velocity of the mandrel is varied during manipulation of the mandrel.

The system of the invention may further comprise a glove box.

The spraying device may be provided with a focusing mechanism that allows selection of the spray width. The spraying device may comprise an atomizer. The spraying device may be configured to spray a polymer suspension.

The processor may be configured, for example, to manipulate the mandrel during spraying to produce a stent having a helical groove in the continuous coating. The processor may be configured to fill the helical groove with a polymer solution. The processor may be configured to repeat the step of spraying one or more liquid streams one or more additional times.

In another of its aspects, the invention provides a method for manufacturing a stent comprising:

(a) spraying one or more polymer solutions onto a mandrel, each liquid stream having a flow rate and a width;

(b) manipulating the mandrel in the one or more liquid streams according to a predetermined pattern of movement of the mandrel to produce a continuous coating of the polymer solutions on the mandrel, the predetermined pattern of movement having a linear movement of the mandrel along a longitudinal axis of the mandrel and further having a rotational movement of the mandrel around the longitudinal axis;

(c) varying at least one of the flow rate of the liquid streams, the width of the liquid streams, a velocity of the linear movement of the mandrel and a rotational velocity of the mandrel during manipulation of the mandrel;

(d) allowing the one or more polymer solutions to cure on the mandrel and produce the stent; and (e) removing the stent from the mandrel.

The step of spraying the one or more polymer solutions onto the mandrel may be repeated one or more additional times. A filament may be embedded in the continuous coating. The filament may be fashioned, for example, into a helix or an undulating helix.

The mandrel may be manipulated in the polymer streams to produce a continuous coating having a helical groove. The helical groove may be filled with a second polymer solution.

One or more drugs may be incorporated into the stent.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1:
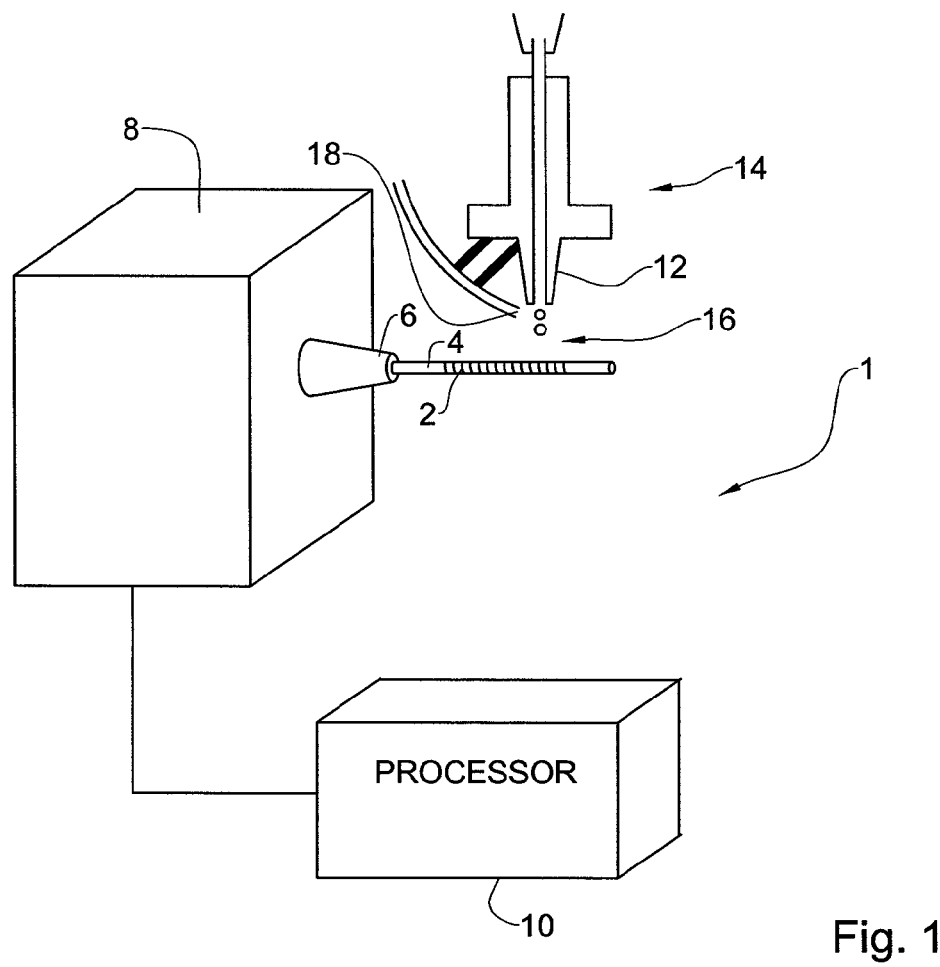
FIG. 1 shows a system for producing a stent in accordance with one embodiment of the system invention.

FIG. 1 shows a system 1 for producing a medical device having an unravable portion in accordance with one embodiment of the invention. The system 1 includes a mandrel 4.

The system 1 also includes a micromanipulator 8. The mandrel 4 is mounted into a chuck 6 of the micromanipulator 8. The micromanipulator 8 is under the control of a programmable processor 10 which is configured to manipulate the mandrel 4 as explained below. The micromanipulator 8 can generate a longitudinal movement of the mandrel 4, as well as rotational movement.

The system 1 further includes an atomizer 14. The mandrel 4 mounted in the chuck 6 is positioned under a nozzle 12 of the atomizer 14. The atomizer 14 applies a coating material such as a polymeric suspension onto the mandrel in the form of an atomized stream 16 of the suspension. The atomizer may be, for example, the AccuMist system of Sono-Tek. In the AccuMist system, an ultrasonically produced spray of the polymeric suspension is produced at the tip of the nozzle 12 and is immediately entrained in a low pressure air stream (typically about 1 psi) from a second nozzle 18. An adjustable focusing mechanism (not shown) allows selection of the spray width which may be, for example, as small as 0.25 mm. The atomizer 14 is also under the control of the processor 10, so that the spraying of the polymer suspension can be coordinated with the manipulation of the mandrel 4 by the micromanipulator 8.

The system 1 is preferably enclosed in a glove box (not shown), in order to isolate the system from external factors such as vibrations and drafts, while allowing a user to monitor the manufacturing process. A low-velocity exhaust (not to shown) may be used to maintain a negative air pressure in the glove-box to remove unwanted polymer suspension beyond the target area.

The coating material may be a polymer such as a urethane, polycarbonate, silicone, or styrene. The solvent of the polymer suspension may be, for example, THF, acetone, DMAC, toluene, or chloroform. After curing of the polymer suspension, the completed stent 26 is removed from the mandrel 4, as shown in FIG. 4. The coating material may be a biodegradable material.

During spraying of the polymeric suspension onto the mandrel 4, the mandrel 4 is manipulated by the micromanipulator 8 under the control of the processor 10 in order to produce a coating on the mandrel 4.

Figure 2:
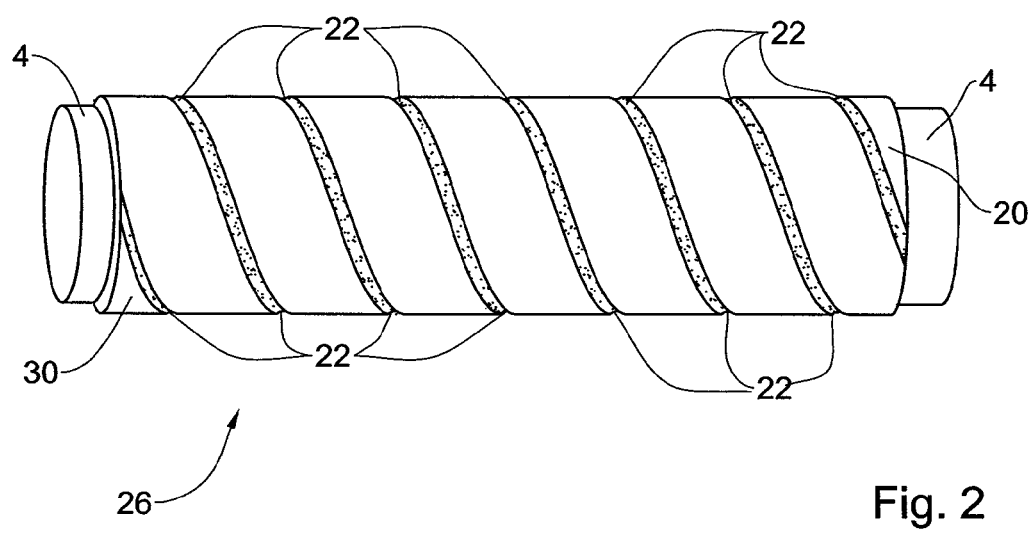
FIG. 2 shows a stent in accordance with one embodiment of the method of the invention.

In one embodiment of the invention, the processor 10 is configured to manipulate the mandrel 4 during spraying of the polymeric suspension so as to produce a stent 26 shown in FIG. 2, having a coating 20 on the mandrel 4 having a surface topography in which there is a shallow helical groove 22. The helical groove 22 in the polymer layer 20 is a weakened region in the coating 20 that forms a tear line that allows the stent to be unraveled by grasping an end 30 of the stent 26 and pulling on the end. When it is desired to remove the stent 22 from the body, the end 30 of the stent can be grasped by a grasping device and pulled. As the end is pulled, the tear line 22 splits so that the stent is removed from the body as a slender strip.

In the manufacture of a medical device by the method of the invention, application of the polymer suspension to the filament may be carried out in a single application step, as described above. Alternatively, two or more application steps may be used, in which at least one of the applications involves spraying polymer suspension, using the system of the invention. For example, a first coat may be sprayed onto the mandrel producing a coating having a smooth outer surface, and then a second coat may be applied having a grooved outer surface. As another example, a first coat of polymer suspension may be applied by dipping the mandrel and filament into a polymer suspension, and then spraying a second coat using the system of the invention. When more than one polymer applications are used, the different coats may be from the same material or from different materials.

Figure 3:
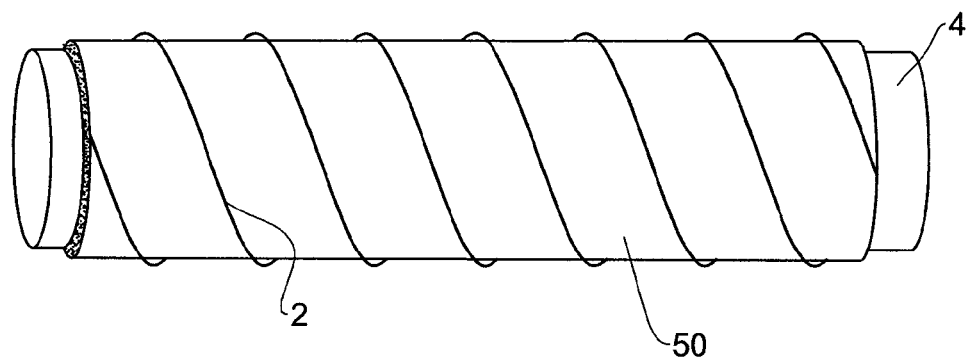
FIG. 3 shows an intermediate step in the production of another stent by the to method of the invention.
Figure 4A:
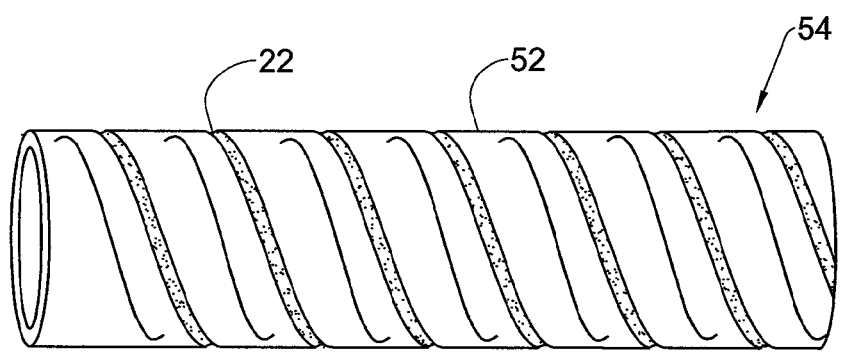
FIG. 4a shows the stent of FIG. 3 in a perspective view after completion and FIG. 4b shows the stent of FIG. 3 in longitudinal section after completion.
Figure 4B:
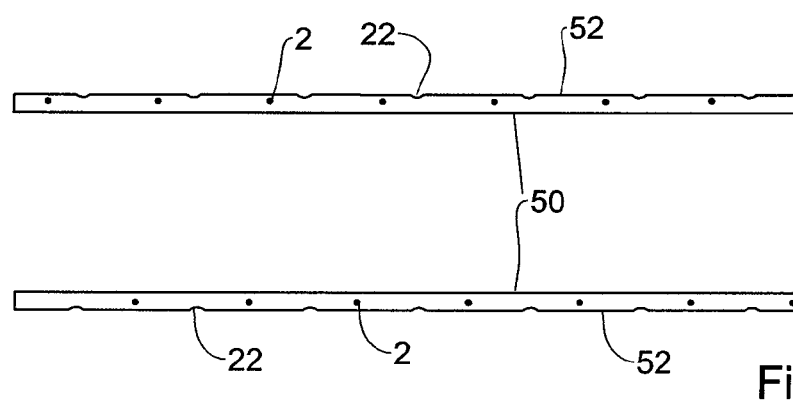

In another embodiment of the invention, shown in FIGS. 3 and 4, a first coating 50 is applied to the mandrel 4 having a smooth outer surface. After curing of the first coating 50, a flexible filament 2 is mounted onto the mandrel 4 over the first coating in a desired shape. The filament may be for example a metal wire from stainless steel or a nickel-titanium alloy (Nitinol). The filament may be made from a biodegradable material. In FIG. 3, the filament 2 has been fashioned into a helix. The wire may also be fashioned into an undulating helix, as disclosed in WO03/099166. A second coating material 52 is then applied over the first coating material that bonds to the first coating material so that the filament 2 becomes embedded between the two coatings. The outer coating 20 has a surface topography in which there is a shallow helical groove 22 with the filament running parallel to the groove that forms a helical tear line. The stent 26 is shown in a perspective view in FIG. 4a and in longitudinal section in FIG. 4b. This process produces a stent 54 shown in perspective view in FIG. 4a, and in longitudinal cross-sectional view in FIG. 4b.

Figure 5A:
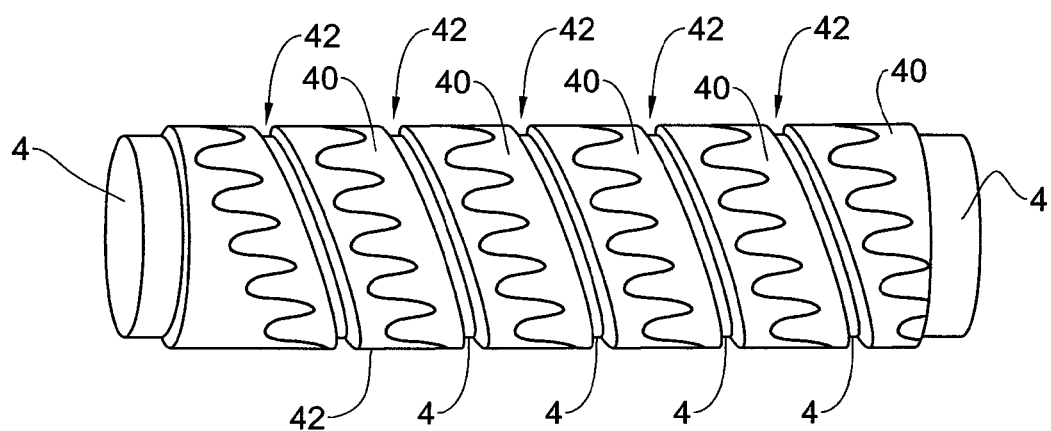
FIG. 5a shows an intermediate step in the production of another stent by the method of the invention.
Figure 5B:
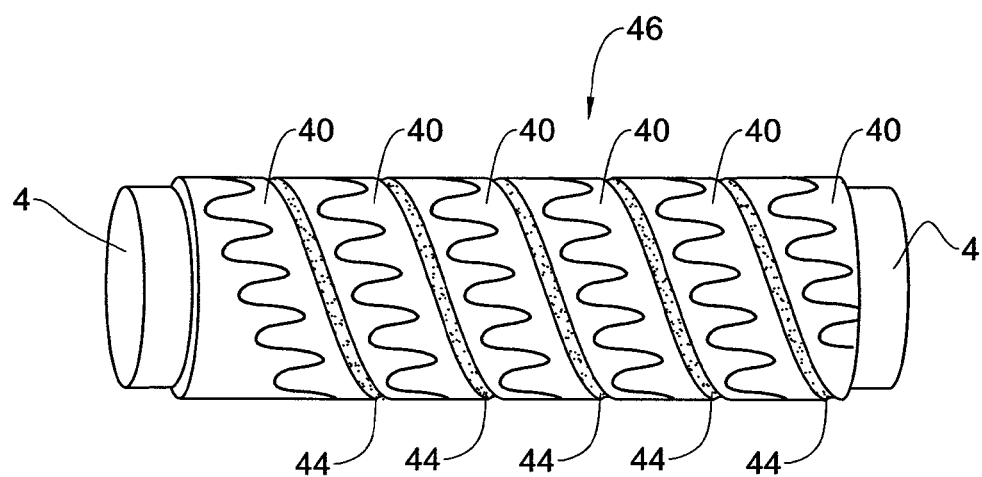
FIG. 5b shows the stent of FIG. 5a in a perspective view after completion.

FIG. 5 shows a method for producing an unravable stent in accordance with another embodiment of the invention. As shown in FIG. 5a, a first coating material such as a polymer suspension is applied to the mandrel 4 so as to form a coating 40 of the mandrel in which a groove 42 is present. A filament may or may not be embedded in the coating 40. The groove 42 may be completely devoid of the coating material, as shown in FIG. 5a, so that after formation of the coating 40 the mandrel 4 is exposed in the grooves 42. Alternatively, the groove may contain a thin layer of the coating so that the thickness of the coating is thinner in the grooves. Then, as shown in FIG. 5b, a second material 44 is sprayed into the grooves 42. The second material 44 is selected to be weaker than the first material 40. A stent 46 is thus formed in which the second material 44 forms a helically shaped tear line. The tear line can be detached by pulling on an end of the stent 46, as explained above.

After formation of the stent of the medical device, the device may be adapted, for example, to contain one or more drugs that are released over time after deployment of the device in the body. For example, a small region of the polymer can be removed and replaced with a plug contain the drug or drugs to be released.

The invention claimed is:

1. A system for manufacturing a stent comprising:
   (a) a spraying device configured to deliver one or more liquid streams, each liquid stream having a flow rate and a width;
   (b) a mandrel having a longitudinal axis, the system configured for linear movement of the mandrel along the longitudinal axis and for rotational movement of the mandrel around the longitudinal axis;
   (c) a micromanipulator configured to grasp the mandrel and to manipulate the mandrel in the one or more liquid streams; and
   (d) a processor configured to
      (i) activate the micromanipulator to manipulate the mandrel in the one or more liquid streams according to a predetermined pattern of movement of the mandrel, the predetermined pattern of movement having a linear movement of the mandrel along the longitudinal axis and further having a rotational movement of the mandrel around the longitudinal axis; and
      (ii) activate the spraying device to spray the one or more liquid streams onto the mandrel as the mandrel is being manipulated in the liquid streams to form a continuous coating over the mandrel;
   wherein at least one of the flow rate of the liquid streams, the width of the liquid streams, a velocity of the linear movement of the mandrel and a rotational velocity of the mandrel is varied during manipulation of the mandrel, and
   wherein the processor is configured to manipulate the mandrel during spraying to produce a stent having a helical groove in the continuous coating, the helical groove defining a weakened region in the stent that forms a tear line.

2. The system according to claim 1, wherein the spraying device is provided with a focusing mechanism that allows selection of the spray width.

3. The system according to claim 1, further comprising a glove box.

4. The system according to claim 1, wherein the spraying device comprises an atomizer.

5. The system according to claim 1, wherein the spraying device is configured to spray a polymer suspension.

6. The system according to claim 1, wherein the processor is further configured to fill the helical groove with a polymer solution.

7. The system according to claim 1, wherein the processor is further configured to repeat the step of spraying one or more liquid streams one or more additional times.

8. A method for manufacturing a stent comprising:
   (a) spraying one or more polymer solutions onto a mandrel, each liquid stream having a flow rate and a width;
   (b) manipulating the mandrel in the one or more liquid streams according to a predetermined pattern of movement of the mandrel to produce a continuous coating of the polymer solutions on the mandrel, the predetermined pattern of movement having a linear movement of the mandrel along a longitudinal axis of the mandrel and further having a rotational movement of the mandrel around the longitudinal axis;
   (c) varying at least one of the flow rate of the liquid streams, the width of the liquid streams, a velocity of the linear movement of the mandrel and a rotational velocity of the mandrel during manipulation of the mandrel;
   (d) allowing the one or more polymer solutions to cure on the mandrel and produce the stent, wherein a processor is configured to manipulate the mandrel during spraying to produce the stent having a helical groove in the continuous coating, the helical groove defining a weakened region in the stent that forms a tear line; and
   (e) removing the stent from the mandrel.

9. The method according to claim 8, wherein the step of spraying the one or more polymer solutions onto the mandrel is repeated one or more additional times.

10. The method according to claim 8, further comprising embedding a filament in the continuous coating.

11. The method according to claim 10, wherein the filament is fashioned into a helix or an undulating helix.

12. The method according to claim 8, wherein the mandrel is manipulated in the polymer streams to produce a continuous coating a having the helical groove.

13. The method according to claim 12, further comprising a step of filing the helical groove with a second polymer solution.

14. The method according to claim 8, further comprising incorporating one or more drugs in the stent.

15. The system according to claim 1, wherein the weakened tear line is such as to allow the stent, after being inserted into a body, to be removed from the body by grasping an end of the stent and as the end is pulled the tear line splits, enabling the stent to be removed from the body as a slender strip.

* * * * *